United States Patent [19]

Mushika et al.

[11] 4,327,101
[45] Apr. 27, 1982

[54] QUINOLINE COMPOUND USEFUL AS ANTIBACTERIAL AGENTS IN WARM-BLOODED ANIMALS

[75] Inventors: Yoshitaka Mushika, Kawanishi; Junichi Tani, Osaka; Totaro Yamaguchi, Yono; Satoshi Ohshima, Iwatsuki, all of Japan

[73] Assignee: Tanabe Seikaku Co., Ltd., Osaka, Japan

[21] Appl. No.: 188,713

[22] Filed: Sep. 19, 1980

[30] Foreign Application Priority Data

Oct. 5, 1979 [JP] Japan .................. 54-129120

[51] Int. Cl.$^3$ .................. A61K 31/47; C07D 215/56
[52] U.S. Cl. .................. 424/258; 546/156
[58] Field of Search .................. 546/156; 424/258

[56] References Cited
U.S. PATENT DOCUMENTS 4,146,625  3/1979  Lee .................. 424/258
4,264,604  4/1981  Sturm .................. 424/258

FOREIGN PATENT DOCUMENTS 2246503  4/1974  Fed. Rep. of Germany ...... 424/258
54-14978  2/1979  Japan .
830832  3/1960  United Kingdom .

*Primary Examiner*—Anton H. Sutto
*Assistant Examiner*—Diana G. Rivers
*Attorney, Agent, or Firm*—Linda G. Bierman; Jordan B. Bierman

[57] ABSTRACT

A quinoline compound of the formula:

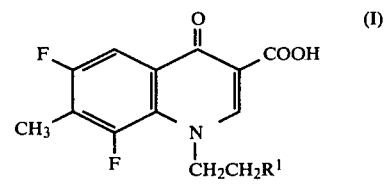

wherein $R^1$ is hydrogen or fluorine. A method of preparing the compound (I) is disclosed. The compound (I) and a pharmaceutically acceptable salt thereof are useful as antimicrobial agents.

5 Claims, No Drawings

QUINOLINE COMPOUND USEFUL AS ANTIBACTERIAL AGENTS IN WARM-BLOODED ANIMALS

This invention relates to a novel quinoline compound and a process for preparing the same. More particularly, it relates to a quinoline compound of the formula:

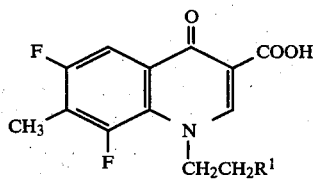

wherein $R^1$ is hydrogen or fluorine, or pharmaceutically acceptable salt thereof.

It is known that 1-ethyl-6-fluoro-, 1-ethyl-7-methyl-, 1-ethyl-6,7-difluoro- and 1-(2,2,2-trifluoroethyl)-6,8-difluoro-derivatives of 4-oxo-1,4-dihydroquinoline-3-carboxylic acid show anti-microbial and/or anti-viral activity (British Patent No. 830,832, Japansese Patent Publication (unexamined) No. 14,978/1979 and U.S. Pat. No. 4,146,625). Among said known compounds, however, the 1-ethyl-6-fluoro- or 1-ethyl-7-methyl-quinoline derivatives disclosed in said British Patent are still unsatisfactory for use in the treatment of infectious diseases because of the weak anti-microbial activity thereof. On the other hand, the Japanese Patent Publication and U.S. patent disclose nothing but that the 1-ethyl-6,7-difluoro- and 1-(2,2,2-trifluoroethyl)-6,8-difluoroquinoline derivatives described above are useful for control of bacterial plant diseases such as fire blight of apple and pear, soft rot of potatoe, and gall formation on herbaceous and woody plants.

The present invention provides novel quinoline compounds which are useful as antibacterial and chemotherapeutic agents in poultry and mammals, including man, in the treatment of infectious diseases caused by gram-positive and gram-negative bacteria. Namely, the quinoline compound (I) of the present invention shows potent antimicrobial activity against a wide variety of microorganisms and at the same time can be effectively absorbed upon either oral or parenteral administration to man and animals. In particular, the quinoline compound (I) shows potent antimicrobial activity against bacteria belonging to the genera Staphylococcus and Pseudomonas. For example, the quinoline compound (I) exhibits minimum inhibitory concentration (M.I.C.) (Agar dilution method, Heart-infusion agar) of 0.78 to 1.56 μg/ml and 6.25 to 12.5 μg/ml against Staphylococcus aureus and Pseudomonas aeruginosa, respectively. The quinoline compound (I) may further exhibit potent antimicrobial activity against other gram-positive and gram-negative bacteria such as those belonging to the genera Proteus, Escherichia, Klebsiella, Salmonella and Shigella. Further, the toxicity of the compound (I) of the present invention is remarkably low. For example, when 1-ethyl-6,8-difluoro-7-methyl-4-oxo-1,4-dihydroquinoline-3-carboxylic acid was administered orally to mice at the dose of 3,000 mg/kg, no mice died during the period of 7 days after the administration.

The quinoline compound (I) of the present invention can be used for pharmaceutical use either as the free acid or a salt thereof. Pharmaceutically acceptable salts of the compound (I) include, for example, non-toxic metallic salts such as sodium, potassium, calcium and magnesium salts; non-toxic amine salts such as dimethylamine, triethylamine, benzylamine and dicyclohexylamine salts; basic amino acid salts such as lysine and arginine salts.

The quinoline compound (I) of the present invention can be administered either orally or parenterally (e.g., intravenously, intramuscularly, subcutaneously). A daily dose of the compound (I) may be about 4 to 40 mg, especially 10 to 20 mg, per kilogram of body weight. Further, the compound (I) may be used in the form of a pharmaceutical preparation containing the same compound in conjunction or admixture with a pharmaceutical excipient suitable for enteral or parenteral administration. Suitable excipients include, for example, gelatin, lactose, glucose, sodium chloride, starch, magnesium stearate, talcum, vegetable oil and other known medicinal excipients. The pharmaceutical preparations may be in solid form such as tablets, pills or capsules; or in liquid form such as solutions, suspensions or emulsions.

The compound (I) of the present invention can be prepared by condensing an alkyl 6,8-difluoro-7-methyl-4-oxo-1,4-dihydroquinoline-3-carboxylate of the formula:

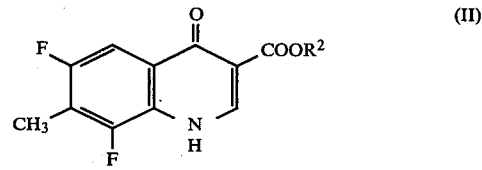

wherein $R^2$ is alkyl of one to five carbon atoms, with an alkyl halide of the formula:

wherein $R^1$ is the same as defined above and X is halogen, to give an alkyl 1-substituted-6,8-difluoro-7-methyl-4-oxo-1,4-dihydroquinoline-3-carboxylate of the formula:

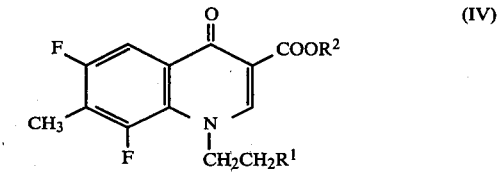

wherein $R^1$ and $R^2$ are the same as defined above, and then hydrolyzing the compound (IV).

In the above-mentioned formulas (II) through (IV), examples of alkyl group ($R^2$) include methyl, ethyl, propyl, isopropyl, butyl, isobutyl, amyl and the like. On the other hand, examples of halogen (X) include bromine, iodine and the like.

The condensation of the compound (II) with the compound (III) is accomplished in the presence of an inorganic or organic base in a solvent. Suitable examples of the base include an alkali metal hydride (e.g., lithium hydride, sodium hydride), an alkyl lithium (e.g., butyl lithium) and the like. Dimethylformamide, dimethylsulfoxide, hexamethylphospholic triamide and the like are suitable as the solvent. It is preferred to carry out the reaction at a temperature of 20° to 70° C.

The hydrolysis of the compound (IV) is accomplished by treating said compound with an acid or an alkali in a solvent. Suitable examples of the acid include mineral acids such as hydrochloric acid or sulfuric acid. On the other hand, suitable examples of the alkali include alkali metal hydroxides such as potassium hydroxide or sodium hydroxide. A mixture of water and alkanol (e.g., methanol, ethanol) is suitable as the solvent. It is preferred to carry out the reaction at a temperature of 10° to 50° C.

The compound (I) thus obtained may be converted into a pharmaceutically acceptable salt thereof in any conventional manner.

The starting compound (II) of the present invention may be prepared by the steps of nitrating 2,6-difluorotoluene (V) to give 2,4-difluoro-3-methyl-nitrobenzene (VI), reducing the compound (VI) to give 2,4-difluoro-3-methylaniline (VII), condensing the compound (VII) with dialkyl alkoxymethylenemalonate (VIII) to give dialkyl 2,4-difluoro-3-methyl-phenylaminomethylenemalonate (IX), and then subjecting the compound (IX) to intramolecular cyclization.

The above-mentioned reactions are shown by the following reaction scheme:

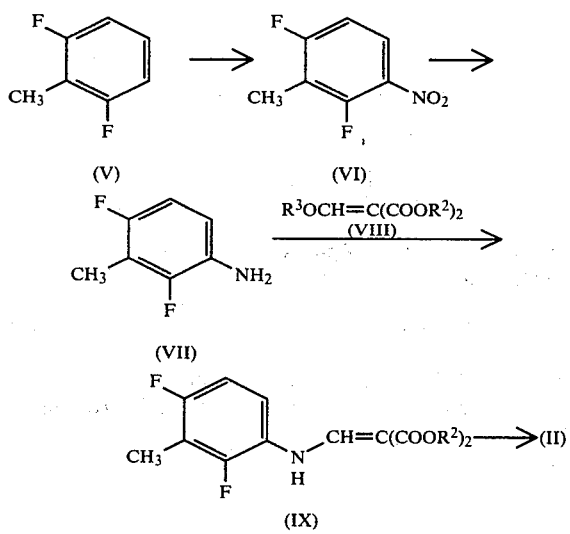

wherein $R^3$ is alkyl of one to four carbon atoms and $R^2$ is the same as defined above.

The nitration of the compound (V) is accomplished by treating said compound with a nitrating agent (e.g., a mixture of an alkali metal nitrate and conc. sulfuric acid). For example, the nitration may be carried out by adding fuming nitric acid or alkali metal nitrate (e.g., potassium nitrate, sodium nitrate) to a suspension of the compound (V) in conc. sulfuric acid, and then stirring the mixture at a temperature of 0° to 30° C. Concomitantly, the compound (V) can be prepared in accordance with the method described in J. Pharm. Pharmaco., 14, 587(1962).

The reduction reaction of the compound (VI) is accomplished by treating said compound with a reducing agent (e.g., stannous chloride-hydrochloric acid) in a suitable solvent (e.g., methanol, ethanol, ether, tetrahydrofuran, dioxane) at a temperature of 0° to 30° C. Alternatively, the reduction reaction of the compound (VI) may be conducted by catalytic hydrogenation. The catalytic hydrogenation can be carried out in hydrogen gas atmosphere in the presence of a catalyst (e.g., palladium-carbon) in a suitable solvent (e.g., tetrahydrofuran, methanol, ethanol, dioxane, diethyl ether, water) at a temperature of 20° to 60° C. under one to 3 atmospheric pressures.

The condensation of the compound (VII) with the compound (VIII) is carried out by heating said both compounds at a temperature of 30° to 150° C., especially around 120° C., in a suitable solvent (e.g., benzene, toluene, xylene) or without said solvent.

The subsequent intramolecular cyclization of the compound (IX) is conducted by heating said compound at a temperature of 200° to 300° C., especially around 250° C., in a suitable solvent (e.g., diphenyl ether, silicone oil, alkylnaphthalene, diethyl futarate, mineral oil).

EXPERIMENT 1

The minimum inhibitory concentration (M.I.C.) (μg/ml) of each of the compounds of the present invention were estimated by conventional agar dilution test in a heart infusion agar medium. A loopful of each test microorganism (pre-cultivated in Trypto-soy broth for 16 hours; 10-fold dilution) were streaked on the above-described agar plates and cultured for 24 hours at 37° C. The results are shown in the following Table.

TABLE

| | M.I.C. (μg/ml) Test compound | |
|---|---|---|
| Microorganisms | A | B |
| Staphylococcus aureus | 0.78–1.56 | 0.78–1.56 |
| Escherichia coli | 0.78 | 0.38 |
| Klebsiella pneumoniae | 0.39–1.56 | 0.39–0.78 |
| Proteus mirabilis | ≦0.1 | ≦0.1 |
| Pseudomonas aeruginosa | 6.25–12.5 | 6.25–12.5 |
| Shigella sonnei | 0.39 | 0.2 |
| Salmonella typhimurium | 0.78 | 0.39 |

Note:
A : 1-ethyl-6,8-difluoro-7-methyl-4-oxo-1,4-dihydroquinoline-3-carboxylic acid
B : 1-(2-fluoroethyl)-6,8-difluoro-7-methyl-4-oxo-1,4-dihydroquinoline-3-carboxylic acid

EXPERIMENT 2

Male ddY-strain mice weighing 18 to 20 g were challenged via the intraperitoneal route with microbial cells of Escherichia coli. Namely, the microbial cells were suspended in 5% musin, and the cell suspension was injected intraperitoneally in the mice at such a challenge dose that all the mice may die within 24 hours. A suspension of a test compound in an aqueous 0.5% carboxymethylcellulose solution was administered orally to the mice one hour after the injection of the microbial cells, and the mice were observed for 7 days. As a result, 1-ethyl-6,8-difluoro-7-methyl-4-oxo-1,4-dihydroquinoline-3-carboxylic acid at a dose of 20 mg/kg and 1-(2-fluoroethyl)-6,8-difluoro-7-methyl-4-oxo-1,4-dihydroquinoline-3-carboxylic acid at a dose of 5 mg/kg were effective to protect the mice from the infectious death.

Practical and presently preferred embodiments of the present invention are illustratively shown in the following Examples.

EXAMPLE 1

(1) 10.25 g of 2,6-difluorotoluene are suspended in 13 ml of conc. sulfuric acid, and 4.1 ml of fuming nitric acid are added dropwise thereto at 20° to 25° C. for about 30 minutes. The mixture is stirred at the same temperature for 1.5 hours. The reaction mixture is poured into 200 g of ice-water. The precipitates are collected by filtration, washed with water and then dried. The brown solid product (13.5 g) thus obtained is distilled under reduced pressure, whereby 9.20 g of 2,4-difluoro-3-methyl-nitrobenzene are obtained. Yield: 66%

B.p. 78°–80° C. (4 mm Hg)

M.p. 35°–38° C.

(2) 17.31 g of 2,4-difluoro-3-methylnitrobenzene are dissolved in 300 ml of ether, and a solution of 90.3 g of stannous chloride dihydrate in 80 ml of conc. hydrochloric acid is added dropwise thereto at a temperature below 0° C. for about one hour. Then, the mixture is stirred at room temperature for 3 hours. After the reaction, 750 ml of water are added to the reaction mixture, and the aqueous mixture is neutralized with sodium bicarbonate. The aqueous layer is separated from the ether layer, and said aqueous layer is extracted with chloroform. The extract and the ether layer are combined, and the combined solution is evaporated to remove solvent. The residue thus obtained is distilled under reduced pressure, whereby 12.10 g of 2,4-difluoro-3-methylaniline are obtained as a pale yellow oil. Yield: 85%

B.p. 72°–74° C. (10 mm Hg)

NMR (CDCl$_3$) δ: 2.18 (3H, t, J=2, CH$_3$), 3.47 (2H, s, NH$_2$), 6.25–6.95 (2H, m, protons in the benzene ring)

(3) 7.15 g of 2,4-difluoro-3-methylaniline are mixed with 10.81 g of diethyl ethoxymethylenemalonate, and the mixture is heated at 120° C. for 30 minutes under reduced pressure (about 25 mm Hg). Then, the mixture is cooled to room temperature, and n-hexane is added to said mixture. The insoluble materials are collected by filtration, and then washed with n-hexane. 13.95 g of diethyl 2,4-difluoro-3-methylphenylaminomethylenemalonate are thereby obtained as crystalline powder. Yield: 89%

M.p. 79° C.–82° C.

The product is recrystallized from diisopropyl ether to give colorless needles.

M.p. 80°–82° C.

NMR (CDCl$_3$) δ: 1.35 (3H, t, J=7, CH$_2$C$\underline{H}_3$), 1.40 (3H, t, J=7, CH$_2$C$\underline{H}_3$), 2.24 (3H, t, J=2, C$\underline{H}_3$), 4.27 (2H, q, J=7, C$\underline{H}_2$CH$_3$), 4.34 (2H, q, J=7, C$\underline{H}_2$CH$_3$), 6.67–7.30 (2H, m, protons in the benzene ring), 8.42 (1H, d, J=14, —N—C$\underline{H}$=), 11.01 (1H, d, J=14, —N$\underline{H}$—C=)

(4) 15.67 g of diethyl 2,4-difluoro-3-methylphenylaminomethylenemalonate are added to 150 ml of diphenyl ether at 250° to 255° C. for 5 to 10 minutes under stirring. The mixture is stirred at the same temperature for 15 minutes, and then cooled to room temperature. The crystalline precipitates are collected by filtration, washed with a mixture of n-hexane and methanol, and then dried. 9.78 g of ethyl 6,8-difluoro-7-methyl-4-oxo-1,4-dihydroquinoline-3-carboxylate are thereby obtained as crystalline powder. Yield: 73%

M.p. 260°–263° C.

The product is recrystallized from dimethylformamide to give colorless needles.

M.p. 273°–275° C.

NMR (CF$_3$COOD) δ: 1.58 (3H, t, J=7, —CH$_2$C$\underline{H}_3$), 2.62 (3H, t, J=2, —C$\underline{H}_3$), 4.75 (2H, q, J=7, —C$\underline{H}_2$CH$_3$), 8.13 (1H, d,d, J=8, J'=2, a proton at the 5th position of the quinoline ring), 9.36 (1H, s, a proton at the 2nd position of the quinoline ring)

(5) 2.67 g of ethyl 6,8-difluoro-7-methyl-4-oxo-1,4-dihydroquinoline-3-carboxylate are suspended in 50 ml of dimethylformamide, and 0.46 g of 66% sodium hydride are added thereto. The suspension is stirred at room temperature until it ceases to release hydrogen gas. 3.12 g of ethyl iodide are added to the suspension, and said suspension is stirred at room temperature for 24 hours and then at 50° to 60° C. for 3 hours. The reaction mixture is condensed to dryness, and water is added to the residue. After stirring the aqueous mixture, insoluble materials are collected by filtration, washed with isopropanol and then dried. 1.95 g of ethyl 1-ethyl-6,8-difluoro-7-methyl-4-oxo-1,4-dihydroquinoline-3-carboxylate are thereby obtained as crystalline powder. Yield: 66%

M.p. 147°–150° C.

The product is recrystallized from isopropanol to give colorless needles.

M.p. 149°–151° C.

NMR (CDCl$_3$) δ: 1.45 (3H, t, J=7, —CH$_2$C$\underline{H}_3$), 1.57 (3H, t, J=7, —CH$_2$C$\underline{H}_3$), 2.37 (3H, t, J=2, —C$\underline{H}_3$), 4.43 (2H, q, J=7, —C$\underline{H}_2$CH$_3$), 4.2–4.6 (2H, m, —C$\underline{H}_2$CH$_3$), 7.95 (1H, d,d, J=9, J'=2, a proton at the 5th position of the quinoline ring), 8.40 (1H, s, a proton at the 2nd position of the quinoline ring)

(6) 2.95 g of ethyl 1-ethyl-6,8-difluoro-7-methyl-4-oxo-1,4-dihydroquinoline-3-carboxylate are suspended in 50 ml of ethanol, and 50 ml of an aqueous 2% sodium hydroxide solution are added thereto. The suspension is stirred at room temperature for 2 hours. Then, the reaction mixture is evaporated to remove solvent, and the residue is adjusted to about pH 1 with 10% hydrochloric acid. The crystalline precipitates are collected by filtration, washed with water and then dried. 2.41 g of 1-ethyl-6,8-difluoro-7-methyl-4-oxo-1,4-dihydroquinoline-3-carboxylic acid are thereby obtained as crystalline powder. Yield: 90%

M.p. 245°–248° C.

The product is recrystallized from dimethylformamide to give pale yellow needles.

M.p. 248°–250° C.

NMR (CF$_3$COOD) δ: 1.83 (3H, t, J=7, —CH$_2$C$\underline{H}_3$), 2.65 (3H, d,d, J=1.5, J'=2.5, C$\underline{H}_3$), 5.14 (2H, d,q, J=7, J'=3, —C$\underline{H}_2$CH$_3$), 8.25 (1H, d,d, J=8, J'=2, a proton at the 5th position of the quinoline ring), 9.36 (1H, s, a proton at the 2nd position of the quinoline ring)

EXAMPLE 2

(1) 2.67 g of ethyl 6,8-difluoro-7-methyl-4-oxo-1,4-dihydroquinoline-3-carboxylate are suspended in 50 ml of dimethylformamide, and 0.46 g of 66% sodium hydride are added thereto. The suspension is stirred at room temperature until it ceases to release hydrogen gas. 2.55 g of 2-fluoroethyl bromide are added to the suspension, and said suspension is stirred at 50° to 60° C. for 44 hours. Then, the reaction mixture is evaporated to remove solvent, and the residue is dissolved in chloroform. The solution is washed with water, dried and then evaporated to remove solvent. The residue thus obtained is purified by silica gel chromatography (Solvent: chloroform), whereby 1.60 g of ethyl 1-(2-fluoroethyl)-6,8-difluoro-7-methyl-4-oxo-1,4-dihydroquinoline-3-carboxylate are obtained as crystalline powder. Yield: 51%

The product is recrystallized from ethanol to give colorless needles.

M.p. 202°–204° C.

NMR (CDCl$_3$) δ: 1.40 (3H, t, J=7, —CH$_2$C$\underline{H}_3$), 2.32 (3H, d,d, J=2, J'=3, —C$\underline{H}_3$), 4.2–5.4 (6H, m, N—C$\underline{H}_2$C$\underline{H}_2$—F, —C$\underline{H}_2$CH$_3$), 7.95 (1H, d,d, J=9, J′=2, a proton at the 5th position of the quinoline ring), 8.33 (1H, s, a proton at the 2nd position of the quinoline ring)

(2) 3.13 g of ethyl 1-(2-fluoroethyl)-6,8-difluoro-7-methyl-4-oxo-1,4-dihydroquinoline-3-carboxylate are suspended in 50 ml of ethanol, and 50 ml of an aqueous 2% sodium hydroxide solution are added thereto. The suspension is stirred at room temperature for 3 hours. Then, the reaction mixture is evaporated under reduced pressure to remove solvent, and the residue is adjusted to about pH 1 with 10% hydrochloric acid. The crystalline precipitates are collected by filtration, washed with water and then dried. 2.85 g of 1-(2-fluoroethyl)-6,8-difluoro-7-methyl-4-oxo-1,4-dihydroquinoline-3-carboxylic acid are thereby obtained as crystalline powder. Yield: 100%

M.p. 215°–217° C.

The product is recrystallized from dimethylacetamide to give colorless needles.

M.p. 218°–220° C.

NMR (CF$_3$COOD) δ: 2.63 (3H, d,d, J=3, J′=2, —CH$_3$), 4.5–5.8 (4H, m, N—C$\underline{H}_2$C$\underline{H}_2$F), 8.28 (1H, d,d, J=8, J′=2, a proton at the 5th position of the quinoline ring), 9.32 (1H, s, a proton at the 2nd position of the quinoline ring)

EXAMPLE 3

One g of 1-ethyl-6,8-difluoro-7-methyl-4-oxo-1,4-dihydroquinoline-3-carboxylic acid is suspended in 100 ml of water, and a solution of 0.15 g of sodium hydroxide in 5 ml of water is added thereto to dissolve said quinoline-3-carboxylic acid therein. The solution is condensed to dryness under reduced pressure, whereby 1.08 g of sodium 1-ethyl-6,8-difluoro-7-methyl-4-oxo-1,4-dihydroquinoline-3-carboxylate are obtained as colorless crystalline powder. Yield: 100%

M.p. 288°–290° C. (decomp.)

What we claim is:

1. A quinoline compound of the formula:

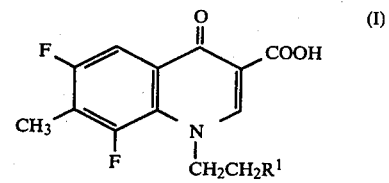

wherein R$^1$ is hydrogen or fluorine, or a pharmaceutically acceptable salt thereof.

2. The compound of claim 1 which is 1-ethyl-6,8-difluoro-7-methyl-4-oxo-1,4-dihydroquinoline-3-carboxylic acid or a pharmaceutically acceptable salt thereof.

3. The compound of claim 1 which is 1-(2-fluoroethyl)-6,8-difluoro-7-methyl-4-oxo-1,4-dihydroquinoline-3-carboxylic acid or a pharmaceutically acceptable salt thereof.

4. An anti bacterial composition comprising an amount of the compound of claim 1 which, when administered to a warm blooded animal, provides an effective amount of said compound, and a pharmaceutically acceptable carrier.

5. The composition of claim 4 wherein said effective amount is 4 to 40 mg/kg per day.

* * * * *